(12) United States Patent
Shur et al.

(10) Patent No.: US 9,034,271 B2
(45) Date of Patent: May 19, 2015

(54) STORAGE DEVICE INCLUDING ULTRAVIOLET ILLUMINATION

(71) Applicant: Sensor Electronic Technology, Inc., Columbia, SC (US)

(72) Inventors: Michael Shur, Latham, NY (US); Maxim Shatalov, Columbia, SC (US); Timothy James Bettles, Columbia, SC (US); Yuri Bilenko, Columbia, SC (US); Saulius Smetona, Concord, NC (US); Alexander Dobrinsky, Providence, RI (US); Remigijus Gaska, Columbia, SC (US)

(73) Assignee: Sensor Electronics Technology, Inc., Columbia, SC (US)

( * ) Notice: Subject to any disclaimer, the term of this patent is extended or adjusted under 35 U.S.C. 154(b) by 0 days.

(21) Appl. No.: 14/012,682

(22) Filed: Aug. 28, 2013

(65) Prior Publication Data

US 2014/0060095 A1  Mar. 6, 2014

Related U.S. Application Data

(60) Provisional application No. 61/694,229, filed on Aug. 28, 2012, provisional application No. 61/694,232, filed on Aug. 28, 2012.

(51) Int. Cl.
*A61L 2/10* (2006.01)
*F25D 27/00* (2006.01)
*F25D 17/04* (2006.01)

(52) U.S. Cl.
CPC .................. *A61L 2/10* (2013.01); *F25D 27/005* (2013.01); *F25D 17/042* (2013.01); *F25D 2317/0417* (2013.01); *A61L 2202/14* (2013.01); *A61L 2202/21* (2013.01)

(58) Field of Classification Search
CPC ... A61L 2/10; A61L 2202/14; A61L 2202/21; F25D 27/005; F25D 17/042
USPC ........................................................ 422/186.3
See application file for complete search history.

(56) References Cited

U.S. PATENT DOCUMENTS 3,817,703 A   6/1974  Atwood
5,364,645 A  11/1994  Lagunas-Solar et al.
(Continued)

FOREIGN PATENT DOCUMENTS

EP        1038536      6/2005
JP     2002204653      7/2002
(Continued)

OTHER PUBLICATIONS

Sharma et al., "Inactivation of *E. coli* O157:H7 on Inoculated alfalfa seeds with pulsed ultraviolet light and response surface modeling", J. Food Science, 2003, 68:1448-1453.

(Continued)

*Primary Examiner* — Kishor Mayekar
(74) *Attorney, Agent, or Firm* — LaBatt, LLC

(57) ABSTRACT

Ultraviolet radiation is directed within an area. Items located within the area and/or one or more conditions of the area are monitored over a period of time. Based on the monitoring, ultraviolet radiation sources are controlled by adjusting a direction, an intensity, a pattern, and/or a spectral power of the ultraviolet radiation generated by the ultraviolet radiation source. Adjustments to the ultraviolet radiation source(s) can correspond to one of a plurality of selectable operating configurations including a storage life preservation operating configuration, a disinfection operating configuration, and an ethylene decomposition operating configuration.

23 Claims, 11 Drawing Sheets

(56) References Cited

U.S. PATENT DOCUMENTS

| | | | |
|---|---|---|---|
| 5,919,422 | A | 7/1999 | Yamanaka et al. |
| 6,565,803 | B1 | 5/2003 | Bolton et al. |
| 6,576,188 | B1 | 6/2003 | Rose et al. |
| 6,579,495 | B1 | 6/2003 | Maiden |
| 6,592,816 | B1 | 7/2003 | Ebel et al. |
| 6,673,137 | B1 | 1/2004 | Wen |
| 6,818,177 | B1 | 11/2004 | Turcotte |
| 7,160,370 | B2 | 1/2007 | Baca et al. |
| 7,296,422 | B2 | 11/2007 | Strohm et al. |
| 7,897,104 | B2 | 3/2011 | Kwon |
| 8,277,734 | B2 | 10/2012 | Koudymov et al. |
| 8,384,047 | B2 | 2/2013 | Shur et al. |
| 2002/0074559 | A1 | 6/2002 | Dowling et al. |
| 2002/0122743 | A1 | 9/2002 | Huang |
| 2002/0176809 | A1 | 11/2002 | Siess |
| 2003/0194692 | A1 | 10/2003 | Purdum |
| 2006/0130498 | A1 | 6/2006 | Joshi et al. |
| 2007/0196235 | A1 | 8/2007 | Shur et al. |
| 2007/0205382 | A1 | 9/2007 | Gaska et al. |
| 2009/0280035 | A1 | 11/2009 | Koudymov et al. |
| 2010/0097013 | A1 | 4/2010 | Inskeep |
| 2010/0296971 | A1* | 11/2010 | Gaska et al. .................. 422/62 |
| 2012/0085116 | A1 | 4/2012 | Maeng et al. |

FOREIGN PATENT DOCUMENTS

| | | |
|---|---|---|
| KR | 1020090074966 | 7/2009 |
| KR | 1020110057773 | 6/2011 |
| KR | 1020120011458 | 2/2012 |

OTHER PUBLICATIONS

Hillegas et al., "Inactivation of *Clostridium sporogenes* in clover honey by pulsed UV-light treatment", Cigr J. AE Sci. Res. Dev., 2003, Manuscript FP 03-009. vol. V. 7, Abstract only.

Jun et al., "Pulsed UV light treatment of corn meal for inactivation of *Aspergillus niger* spores", Int. J. Food Sci. Technology., 2003, 38:883-888.

Chisari et al., "Improving the quality of fresh-cut melon through inactivation of degradative oxidase and pectinase enzymatic activities by UV-C treatment", in Food Science & Technology, 46, 463-468, year 2011.

Ozer et al, "Inactivation of *Escherichia coli* O157:H7 and *Listeria monocytogenes* inoculated on raw salmon fillets by pulsed-UV light treatment", International Journal of Food Science and Technology, 2006, 41 (4): 354-360.

Kennedy et al., "An Investigation of the thermal inactivation of *Staphylococcus aureus* and the potential for increased thermotolerance as a result of chilled storage", Journal of Applied Microbiology, 2005, 99, 1229-1235.

Krishnamurthy et al., "Inactivation of *Taphylococcus aureus* in milk using flow-through pulsed UV-light treatment system", Journal of Food Science, 2007, 72 (7) M233-M239.

Bialka et al., "Decontamination of *Escherichia coli* O157:H7 and *Salmonella enterica* on blueberries using ozone and pulsed UV-Light", Journal of Food Science, 2007, 72 (9): M391-M396.

Bialka et al., "Modeling the inactivation of *Escherichia coli* O157:H7 and *Salmonella enterica* on raspberries and strawberries resulting from exposure to ozone or pulsed UV-light", Journal of Food Engineering, 2008, 85 (3): 444-449.

Bialka et al., "Pulsed UV-light penetration of characterization and the inactivation of *Escherichia coli* K12 in solid model systems", Transactions of the ASABE, 2008, 51(1): 195-204. Abstract only.

Bialka et al., "Efficacy of Pulsed UV-Light for the Decontamination of *Escherichia coli* O157:H7 and *Salmonella* spp. on Raspberries and Strawberries", Journal of Food Science, 2008, 73(5):M201-M207.

Krishnamurthy et al., "Inactivation of *Staphylococcus aureus* in milk and milk foam by pulsed UV-light treatment and surface response modeling", Transactions of the ASABE, 2008, 51(6): 2083-2090. Abstract only.

Demirci et al., "Pulsed ultraviolet light", Food Science and Technology International, 14:443-446.

Krishnamurthy et al., "Microscopic and spectroscopic evaluation of inactivation of *Staphylococcus aureus* by pulsed UV light and infrared heating", Food Bioprocess Technol. In-Print, 2008, DOI 10.1007/s11947-008-0084-8, pp. 93-104.

Krishnamurthy et al., Food Processing Operations and Modeling, 2nd edition, 2008, CRC Press, Ch. 11, pp. 281-302.

Zhang et al., Nonthermal Processing Technologies for Food, Chapters 18 and 19, 2011, pp. 249-270.

Demirci et al., "Disinfection of water by flow-through Pulsed ultraviolet light sterilization system", Ultrapure Water Journal, 2007, Abstract.

Krishnamurthy et al., "Inactivation of *Staphylococcus aureus* by pulsed UV-light treatment", J. Food Prot., 2004, Abstract.

Kim, International Search Report for PCT/US2013/057077, Nov. 8, 2013, 10 pages.

Yang, International Search Report for PCT/US2013/056997, Nov. 28, 2013, 12 pages.

Yang, International Search Report for PCT/US2013/056986, Nov. 29, 2013, 12 pages.

Yang, International Search Report for PCT/US2013/056983, Dec. 19, 2013, 12 pages.

Chang, et al., "Removal of Ethylene and Secondary Organic Aerosols Using UV-C 254+185 nm with $TiO_2$ Catalyst", Aerosol and Air Quality Research, 2013, 13:618-626.

Cheba, et al., "Inactivation of *E. coli* Cell Viability and DNA Photobreakage by Pulsed Nitrogen Laser Radiation", CP748 Modern Trends in Physics Research, 2005, 264-267, American Institute of Physics.

Stoffa, Office Action for U.S. Appl. No. 14/012,644, Mar. 10, 2014, 30 pages.

Stoffa, Final Office Action for U.S. Appl. No. 14/012,644, Jul. 3, 2014, 18 pages.

Stoffa, Office Action for U.S. Appl. No. 14/012,644, Aug. 28, 2013, 19 pages.

\* cited by examiner

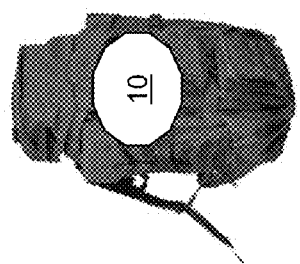
FIG. 4A
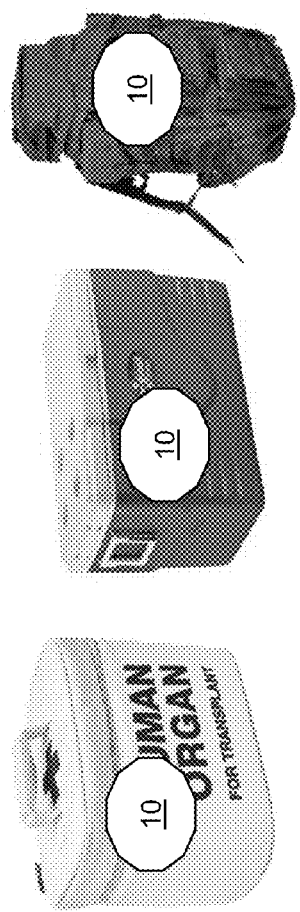
FIG. 4B
FIG. 4C
FIG. 4D
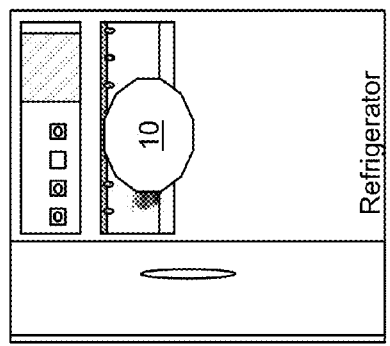
FIG. 4E  FIG. 4F  FIG. 4G
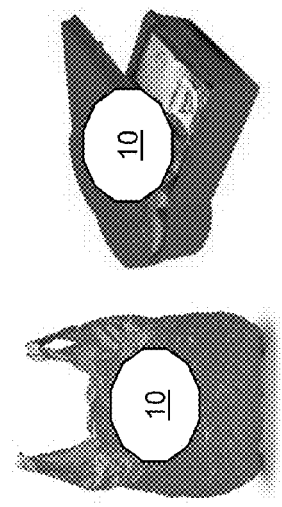
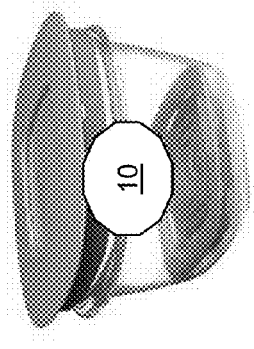
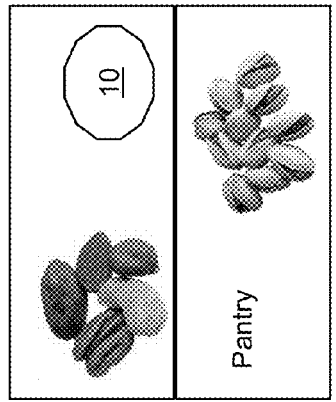
FIG. 4H

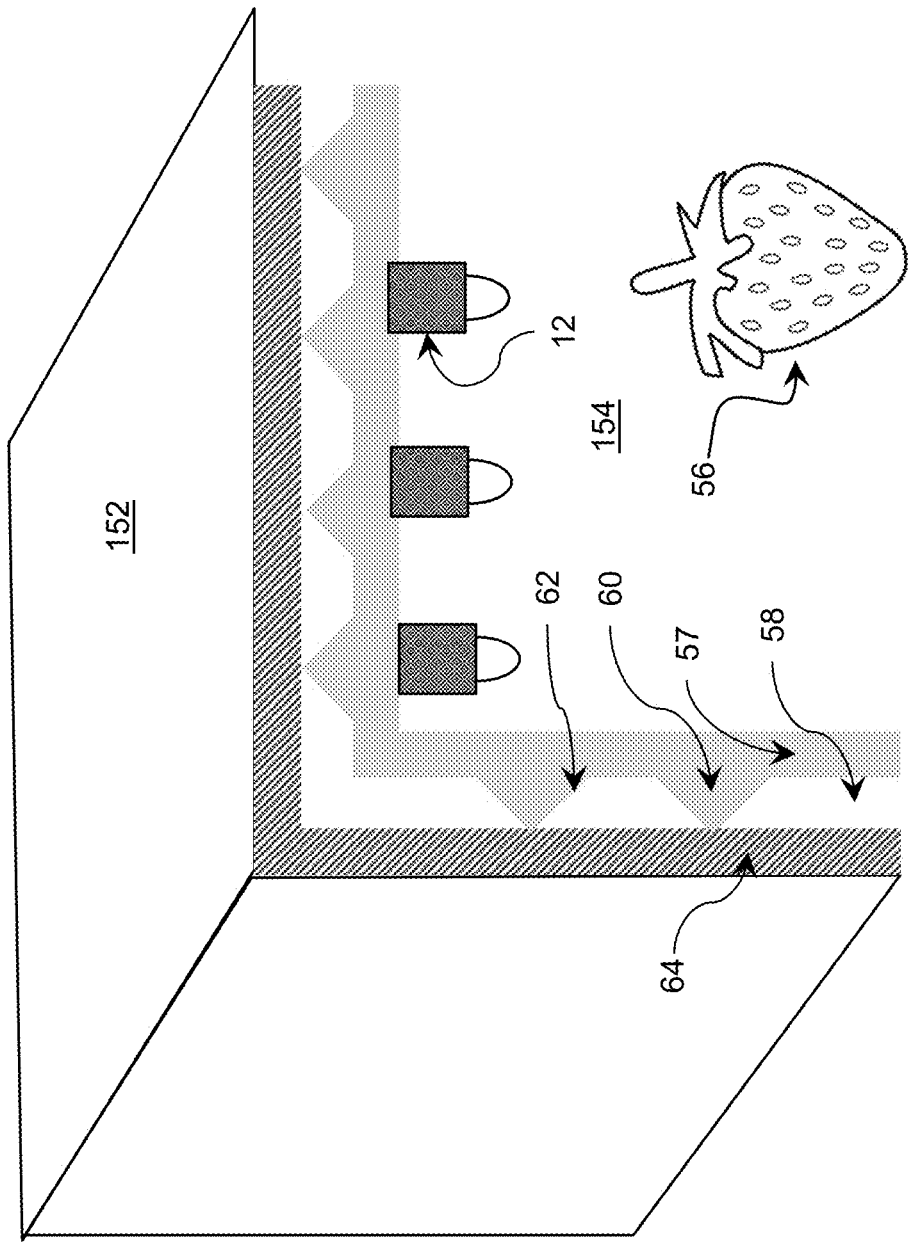

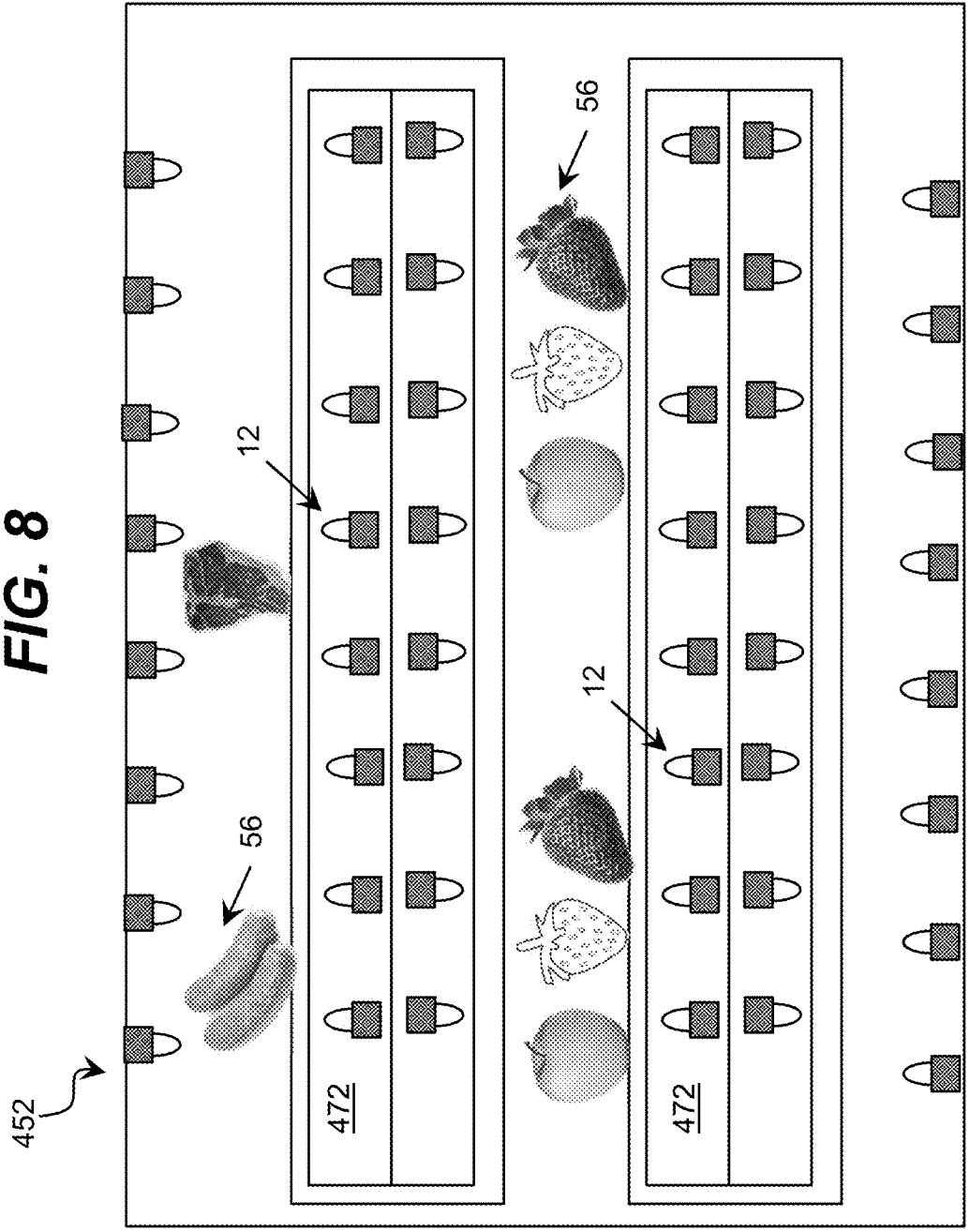

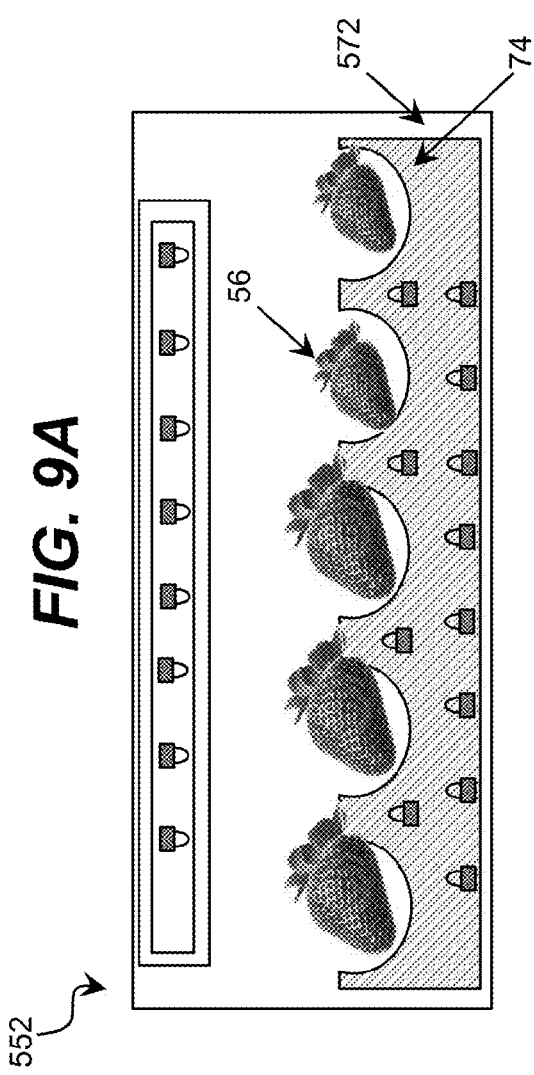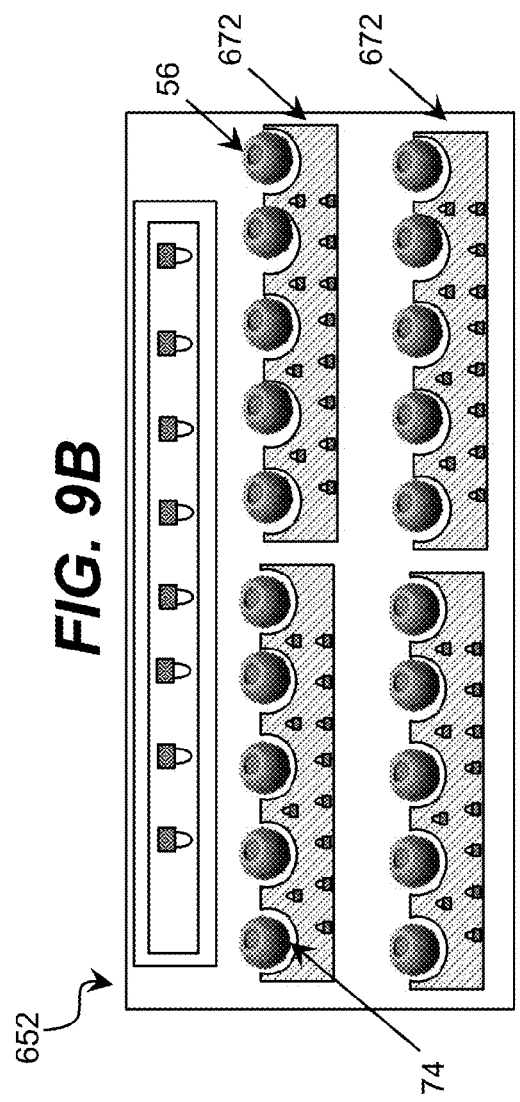

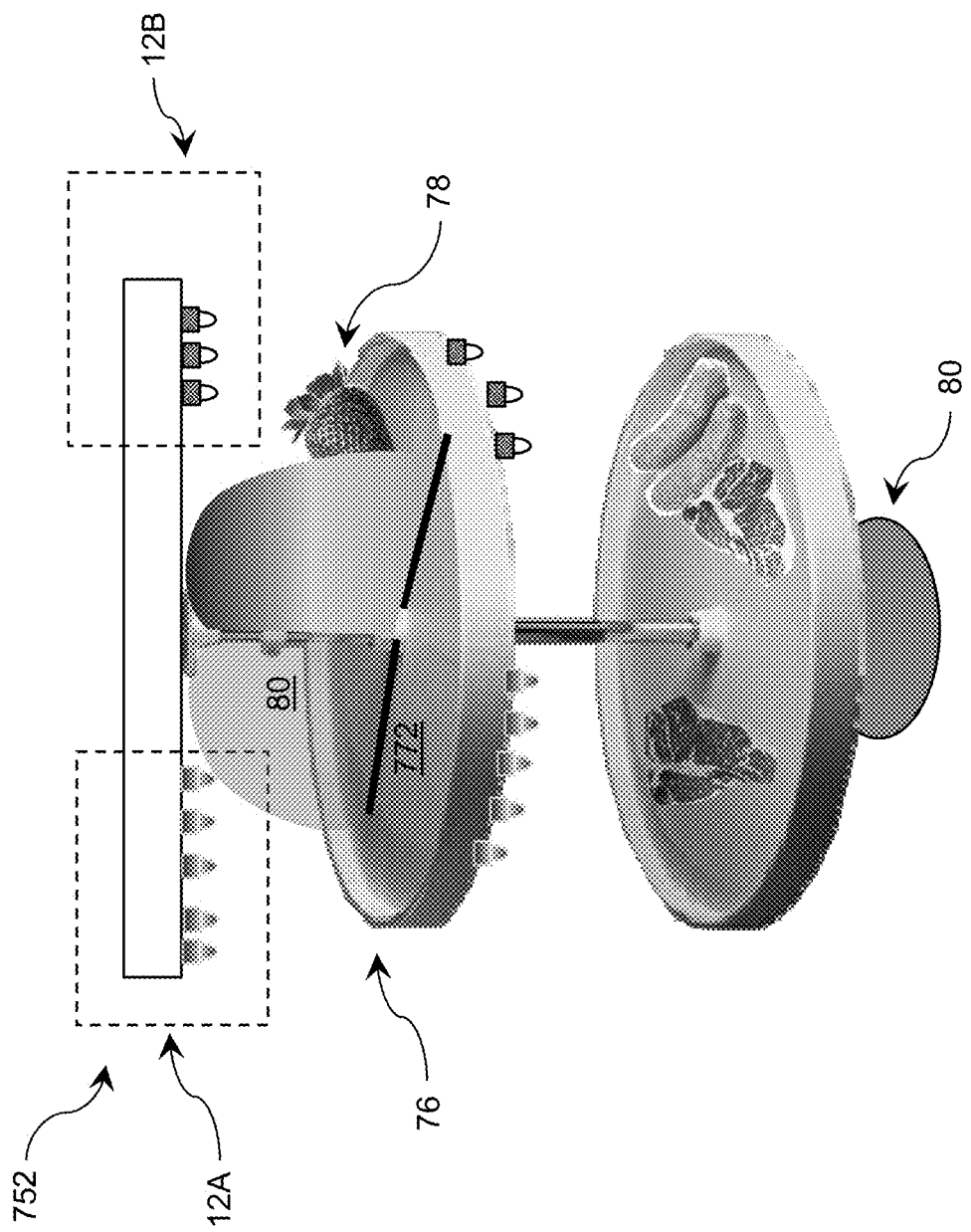

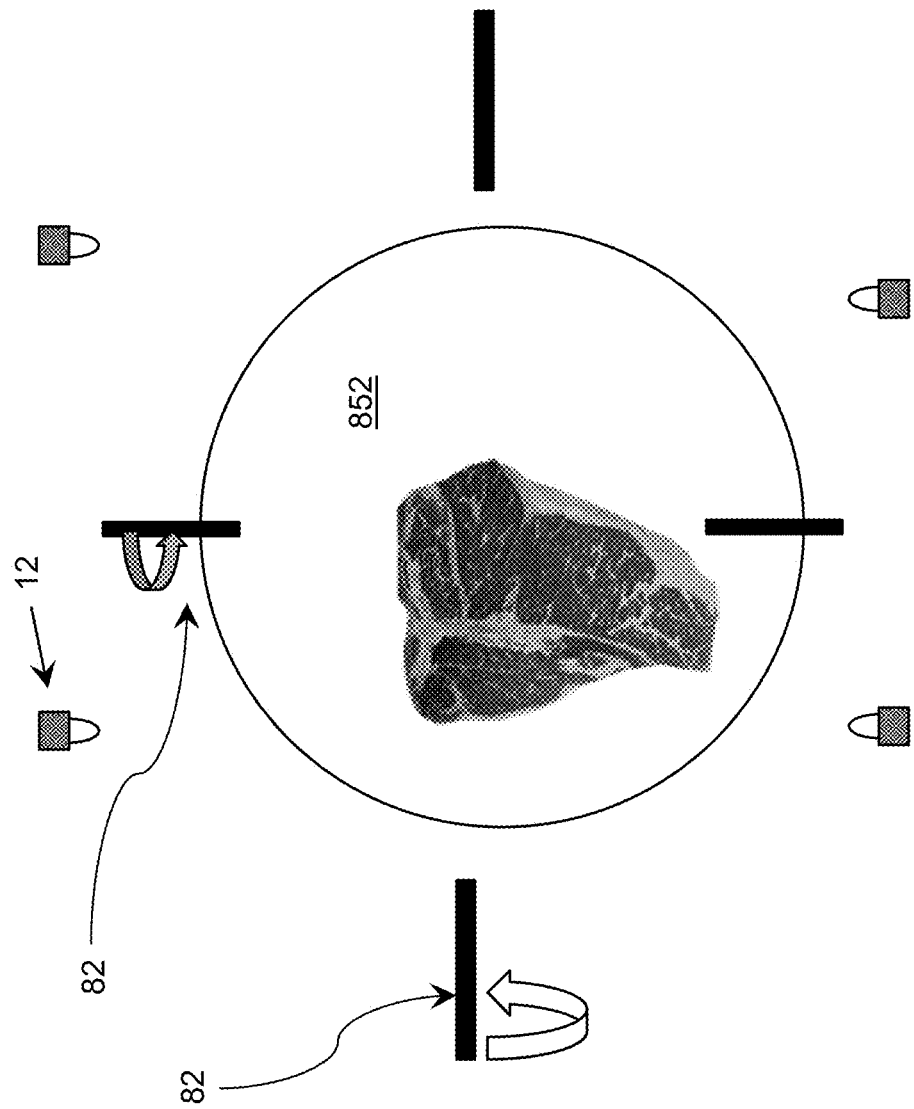

STORAGE DEVICE INCLUDING ULTRAVIOLET ILLUMINATION

REFERENCE TO RELATED APPLICATIONS

The current application claims the benefit of U.S. Provisional Application No. 61/694,229, titled "Compartment for Food Storage Using Ultraviolet Illumination", which was filed on 28 Aug. 2012, and U.S. Provisional Application No. 61/694,232, titled "Ultraviolet System for Preservation of Food Stock", which was filed on 28 Aug. 2012, both of which are hereby incorporated by reference.

TECHNICAL FIELD

The disclosure relates generally to ultraviolet radiation, and more particularly, to a solution for preserving, disinfecting, and/or the like, stored items within an area, such as food items located in a storage area of a refrigerated unit, using ultraviolet radiation.

BACKGROUND ART

Reliable, hygienic storage of sanitary and biological items, such as food, is a major problem. For example, the problem is present throughout the food industry, e.g., manufacturers, retailers, restaurants, and in every household, and is especially significant for food service establishments, in which related issues of food quality control also are significant. In addition to food storage and quality control in fixed locations (e.g., a refrigerator) where access to electricity is readily available, proper food storage and quality control also is important in situations for which access to unlimited electricity and/or a stationary storage device, such as a refrigerator, is not available, such as picnics, camping, mobile food kiosks, hospitality or battlefield meal locations, search and rescue, etc. In addition to food, other stored items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

Fresh food products can be processed using ultraviolet light as a germicidal medium to reduce the food-born microbial load. Water has been treated with ultraviolet light to provide safe drinking water for quite some time. Fruit and vegetable products capable of being pumped through a system generally are very suitable for processing by ultraviolet light to reduce the microbial load. Today, most of these products are pasteurized to obtain microbiologically safe and nutritious products. However, pasteurization can change the taste and flavor of such products because of the temperature and processing time. Juices from different sources can be treated by exposure to ultraviolet light at different doses. On the other hand, variables such as exposure time, type of fruit product, juice color and juice composition, among other variables, need to be studied to obtain fruit products with reduced microbial load, increased shelf life and adequate sensory and nutritional characteristics. Reduction of microbial load through ultraviolet light application as a disinfection medium for food products other than liquids also is being studied. Moreover, ultraviolet technology could be a source for pasteurization of liquids, or disinfection of solid foods as an alternative technology, instead of thermal treatment or application of antimicrobial compounds.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Various approaches have sought to use ultraviolet light to disinfect a compartment, such as compartments found in refrigerators. For example, one approach proposes a plurality of small, low current UV lights which utilize the standard circuitry of the refrigerator to power the UV light source. Another approach uses a UV lamp installed in a top portion of the refrigerator and reflective lining throughout the interior to reflect the UV radiation throughout the compartment. Another approach provides a UV system with a single UV source attached to an internal sidewall of a refrigerator to radiate light to the entire compartment, or in the alternative, provide UV exposure to a limited compartment. Still another approach proposes an air cleaner for an internal compartment of a refrigerator, which utilizes a UV filter to reduce pathogens in the re-circulated air. Still another approach provides a refrigerator with UV light irradiation components to eradicate low-level light from the storage containers contained therein to promote freshness of foodstuffs.

SUMMARY OF THE INVENTION

While refrigerators have been widely used to maintain the freshness of foods stored therein, and several approaches for using UV light devices in connection with refrigerators have been proposed, the inventors recognize that these approaches fail to adequately address food life prolongation, disinfection, ethylene decomposition, and/or the like, through the use of UV source(s), such as UV light emitting diode(s), capable of emitting UV radiation of different wavelengths and/or intensities.

The inventors provide a solution for preserving, disinfecting, and/or the like, stored items within a storage area, such as a storage area of a refrigerated unit, using ultraviolet radiation. For example, an embodiment of the solution is configured to monitor biodegradable items within the storage area and determine and apply a target amount of ultraviolet radiation to preserve and/or disinfect the items, without affecting the quality of the items. Embodiments of the system can be implemented in any of various types of storage environments, such as refrigerators, pantries, reusable grocery bags, coolers, boxes, biological and/or sterile object storage containers, and/or the like.

Aspects of the invention provide a solution in which ultraviolet radiation is directed within an area. Items located within the area and/or one or more conditions of the area are monitored over a period of time. Based on the monitoring, ultraviolet radiation sources are controlled by adjusting a direction, an intensity, a pattern, and/or a spectral power of the ultraviolet radiation generated by the ultraviolet radiation source. Adjustments to the ultraviolet radiation source(s) can correspond to one of a plurality of selectable operating configurations including a storage life preservation operating configuration, a disinfection operating configuration, an ethylene decomposition operating configuration, and/or the like.

A first aspect of the invention provides a system comprising: at least one ultraviolet radiation source configured to generate ultraviolet radiation directed within a storage area; and a control system for controlling ultraviolet radiation generated by the at least one ultraviolet radiation source using one of a plurality of selectable operating configurations and a set of current conditions of at least one of: the storage area or a set of items located in the storage area, wherein the controlling includes adjusting at least one of: a direction, an intensity, a pattern, or a spectral power of ultraviolet radiation directed within the storage area based on the set of current conditions of the storage area and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration.

A second aspect of the invention provides a food storage device comprising: a storage area configured to store at least one perishable food item; at least one ultraviolet radiation source configured to generate ultraviolet radiation directed within the storage area; and a monitoring system for monitoring a set of current conditions of at least one of: the storage area or a set of items located in the storage area, wherein the set of current conditions includes a set of current biological conditions of the storage area and an operating condition of the at least one ultraviolet radiation source.

A third aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using one of a plurality of selectable operating configurations and the set of current conditions, wherein the controlling includes adjusting at least one of: a direction, an intensity, a pattern, or a spectral power of ultraviolet radiation directed within the storage area based on the set of current conditions of the storage area and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 4A-4H show illustrative storage devices for use with an ultraviolet radiation system according to embodiments.

FIG. 5 shows a partial cross-sectional perspective view of an illustrative storage device according to an embodiment.

FIG. 8 shows a cross-sectional view of an illustrative storage device according to an embodiment.

FIGS. 9A and 9B show cross-sectional views of illustrative storage devices according to embodiments.

FIG. 10 shows a perspective view of an illustrative storage device according to an embodiment.

FIG. 11 shows a perspective view of an illustrative storage device according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which ultraviolet radiation is directed within an area. Items located within the area and/or one or more conditions of the area are monitored over a period of time. Based on the monitoring, ultraviolet radiation sources are controlled by adjusting a direction, an intensity, a pattern, and/or a spectral power of the ultraviolet radiation generated by the ultraviolet radiation source. Adjustments to the ultraviolet radiation source(s) can correspond to one of a plurality of selectable operating configurations including a storage life preservation operating configuration, a disinfection operating configuration, an ethylene decomposition operating configuration, and/or the like. As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through.

Figure 1:
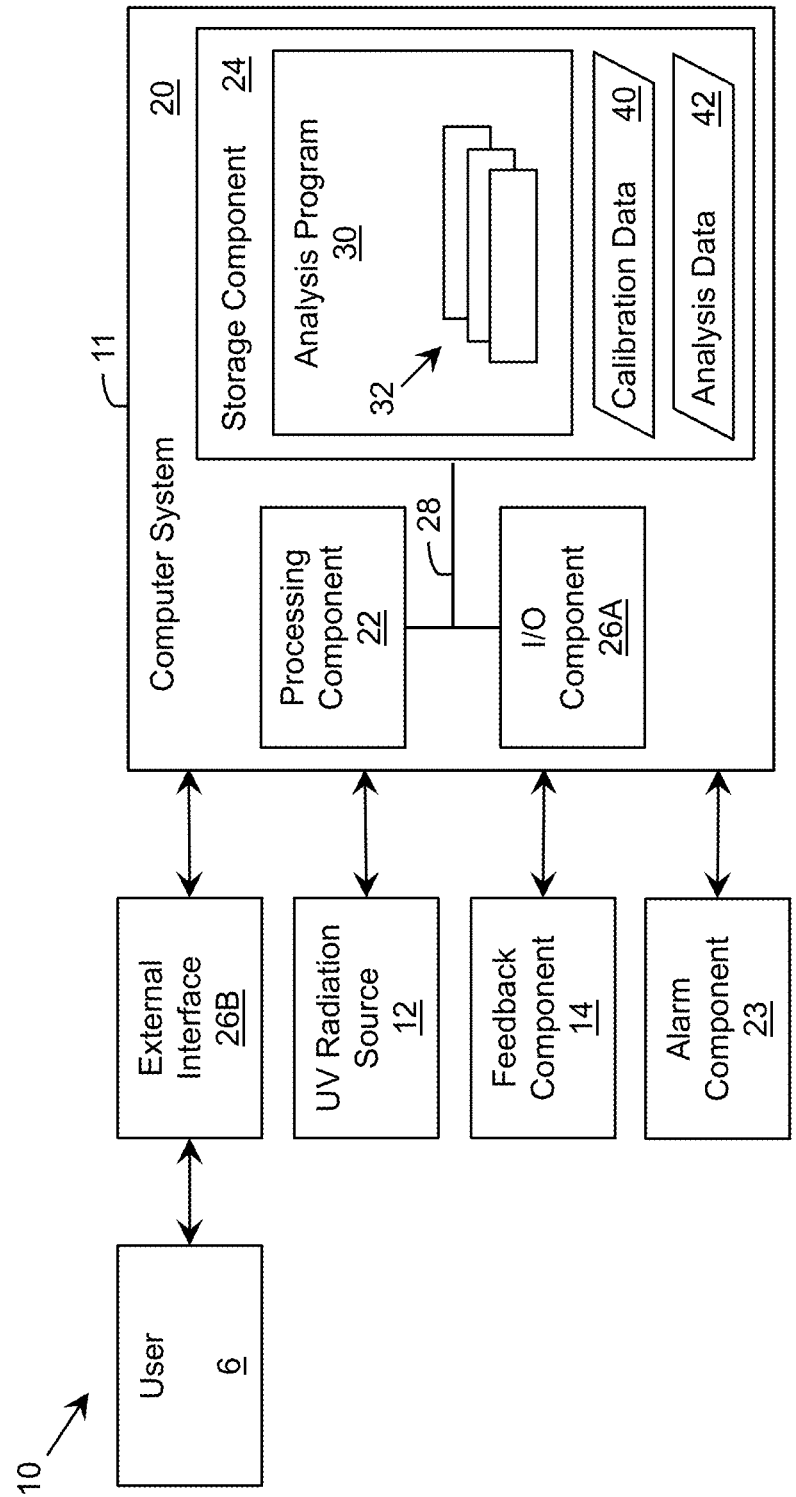
FIG. 1 shows an illustrative ultraviolet radiation system according to an embodiment.

Turning to the drawings, FIG. 1 shows an illustrative ultraviolet radiation system 10 according to an embodiment. In this case, the system 10 includes a monitoring and/or control system 11, which is implemented as a computer system 20 including an analysis program 30, which makes the computer system 20 operable to manage an ultraviolet (UV) radiation source 12 by performing a process described herein. In particular, the analysis program 30 can enable the computer system 20 to operate the UV radiation source 12 to generate and direct ultraviolet radiation within an area and process data corresponding to one or more conditions of the area and/or an item located in the area, which is acquired by a feedback component 14. While a single UV radiation source 12 is shown, it is understood that the area can include any number of UV radiation sources 12, the operation of which the computer system 20 can separately manage using a process described herein.

In an embodiment, during an initial period of operation (e.g., after recent access to the area, addition/removal/reconfiguration of item(s) placed within the area, and/or the like), the computer system 20 can acquire data from the feedback component 14 regarding one or more attributes of the items in the area and/or conditions of the area and generate analysis data 42 for further processing. The analysis data 42 can include information on the color, appearance, and/or the like, of items in the area, the presence of microorganisms on the items or within the area, and/or the like. Furthermore, the analysis data 42 can include information on the presence of ethylene gas within the area. The computer system 20 can use the analysis data 42 to generate calibration data 40 for controlling one or more aspects of the ultraviolet radiation generated by the ultraviolet radiation source(s) 12 using one of a plurality of selectable operating configurations as discussed herein. Furthermore, one or more aspects of the operation of the ultraviolet radiation source 12 can be controlled by a user 6 via an external interface component 26B.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 6 to interact with the computer system 20 and/or one or more communications devices to enable a system user 6 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 6 to interact with the analysis program 30. Furthermore, the analysis program 30 can manage (e.g., store, retrieve, create, manipulate, organize, present, etc.) the data, such as calibration data 40 and analysis data 42, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 11 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 11.

Regardless, when the computer system 20 includes multiple computing devices, the computing devices can communicate over any type of communications link. Furthermore, while performing a process described herein, the computer system 20 can communicate with one or more other computer systems, such as the user 6, using any type of communications link. In either case, the communications link can comprise any combination of various types of wired and/or wireless links; comprise any combination of one or more types of networks; and/or utilize any combination of various types of transmission techniques and protocols. This communications link, which can include a wireless or cable based transmission, can be utilized to transmit information about the state of one or more items and/or zones within the storage area 54.

The system 10 can be implemented within an existing storage device (e.g., a refrigerator) using any solution. For example, one or more ultraviolet radiation sources 12 and one or more devices included in a feedback component 14 can be fixed within various locations in the storage device (e.g., on walls, shelves, etc.) and configured for operation by the computer system 20. The locations of devices in the ultraviolet radiation source(s) 12 and/or the feedback component 14 can be selected to provide comprehensive coverage of the storage area of the storage device and the items located within the storage area. In an embodiment, the computer system 20 can be located outside of the storage area of the storage device.

The ultraviolet radiation source 12 can comprise any combination of one or more ultraviolet radiation emitters. For example, the UV source 12 can include a high intensity ultraviolet lamp (e.g., a high intensity mercury lamp), an ultraviolet light emitting diode (LED), and/or the like. In an embodiment, the UV source 12 includes a set of light emitting diodes manufactured with one or more layers of materials selected from the group-III nitride material system (e.g., $Al_xIn_yGa_{1-x-y}N$, where $0 \leq x, y \leq 1$, and $x+y \leq 1$ and/or alloys thereof). Additionally, the UV source 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the storage area. Illustrative wave guiding structures include, but are not limited to, a plurality of ultraviolet fibers, each of which terminates at an opening, a diffuser, and/or the like. The computer system 12 can independently control each UV source 12.

The system 10 also can include an alarm component 23, which can be operated by the computer system 20 to indicate when ultraviolet radiation is being directed within the storage area. The alarm component 23 can include one or more devices for generating a visual signal, an auditory signal, and/or the like. For example, in the example shown in FIG. 4A, where the storage device 52 includes a refrigeration device, a panel 8 can display a flashing light, text, an image, and/or the like, to indicate that ultraviolet radiation is currently being directed into a corresponding storage area 54. Furthermore, the alarm component 23 can generate a noise, such as a bell, a beep, and/or the like, to indicate that ultraviolet radiation is currently being directed to the storage area 54.

Figure 2:
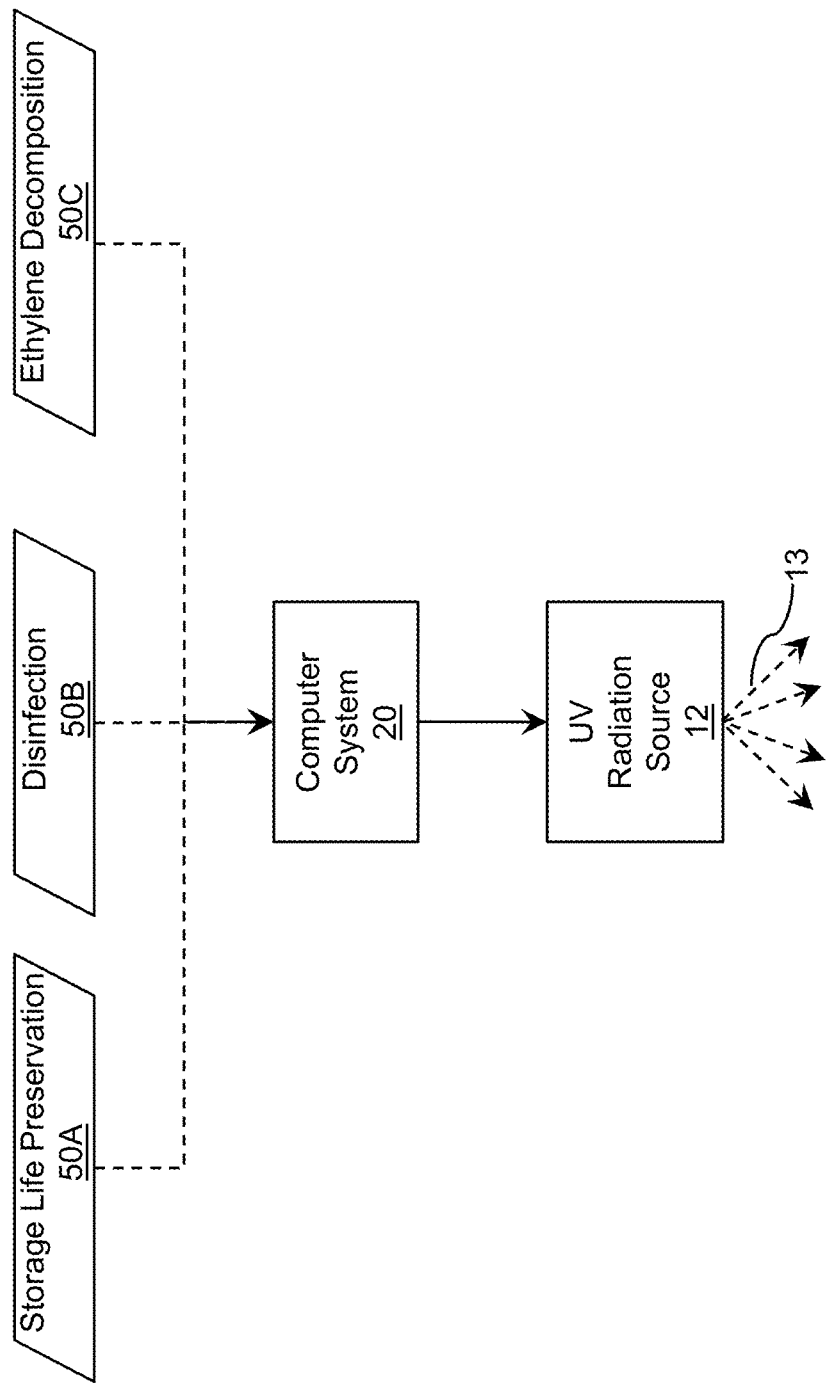
FIG. 2 shows a block diagram illustrating use of operating configurations for operating an ultraviolet radiation source according to an embodiment.

FIG. 2 shows a block diagram illustrating use of operating configurations for operating an ultraviolet radiation source 12 according to an embodiment. As illustrated, the computer system 20 can use data corresponding to a selected operating configuration 50A-50C to adjust one or more aspects of the ultraviolet radiation 13 generated by the ultraviolet radiation source(s) 12. In an embodiment, the operating configurations 50A-50C can include a storage life preservation operating configuration 50A, a disinfection operating configuration 50B, and an ethylene decomposition operating configuration 50C. In an embodiment, the storage life preservation operating configuration 50A is configured to increase a storage lifespan of items stored within the area, while the disinfection operating configuration 50B is configured to eliminate and/or decrease an amount of microorganisms present within the area or on item(s) located within the area. The ethylene decomposition operating configuration 50C can be configured to remove ethylene from the atmosphere of the storage area, which would otherwise decrease the storage lifespan of items located within the area. One or more of these operating configurations can be configured to improve and/or maintain the visual appearance and/or nutritional value of the items within the storage area. For example, increasing the storage lifespan can include suppressing microorganism growth, maintaining and/or improving nutritional value, maintaining and/or improving visual appearance, and/or the like. Also, the operating configurations can be configured to prevent the build-up of mold within the storage area and/or on the items within the storage area.

The computer system 20 is configured to control and adjust a direction, an intensity, a pattern, and/or a spectral power (e.g., wavelength) of the ultraviolet radiation sources 12 to correspond to a particular operating configuration 50A-50C. The computer system 20 can control and adjust each property of the UV source 12 independently. For example, the computer system 20 can adjust the intensity, the time duration, and/or time scheduling (e.g., pattern) of the UV source 12 for a given wavelength. Each operating configuration 50A-50C can designate a unique combination of: a target ultraviolet wavelength, a target intensity level, a target pattern for the ultraviolet radiation (e.g., time scheduling, including duration (e.g., exposure/illumination time), duty cycle, time between exposures/illuminations, and/or the like), a target spectral power, and/or the like, in order to meet a unique set of goals corresponding to each operating configuration 50A-50C.

For example, the storage life preservation operating configuration 50A can require an ultraviolet wavelength of approximately 290 nm peak emission of a relatively lower intensity substantially continuous radiation. For example, an illustrative intensity range can be between approximately 0.1 milliwatt/$m^2$ and approximately 1000 milliwatt/$m^2$. In an embodiment, the intensity for the ultraviolet radiation in the storage life preservation operating configuration 50A can be approximately 400 microwatts/$cm^2$. In a more specific illustrative embodiment, the ultraviolet LEDs can direct ultraviolet radiation having an intensity of a few (e.g., 1-3) microwatts/$cm^2$ for approximately seven days within an enclosure that does not allow ultraviolet radiation to escape, such as an aluminum tube.

The disinfection operating configuration 50B can require any subset of ultraviolet wavelengths in the range of ultraviolet wavelengths (e.g., between approximately 10 nm and approximately 400 nm) and higher intensity levels. In an embodiment, the intensity range can be between approximately 1 milliwatt/$m^2$ and approximately 10 watt/$m^2$. In a more specific embodiment, the ultraviolet wavelength and intensity levels for the disinfection operating configuration 50B can be between approximately 250-290 nm and approximately 20 microwatt/$cm^2$ or higher, respectively, and the ultraviolet light can be applied for approximately 20 minutes. In this case, the dosage of ultraviolet radiation for the disinfection operating configuration 50B can be approximately 24 milliJoule/$cm^2$. However, it is understood that this is only illustrative and a dosage can be at least approximately 16 milliJoule/$cm^2$. The ethylene decomposition operating configuration 50C can require even higher intensity levels and the disinfection operating configuration 50B and a relatively low ultraviolet wavelength of approximately 230-270 nm. In an embodiment, the intensity range can be between approximately 1 milliwatt/$m^2$ and approximately 1000 watt/$m^2$.

Figure 3:
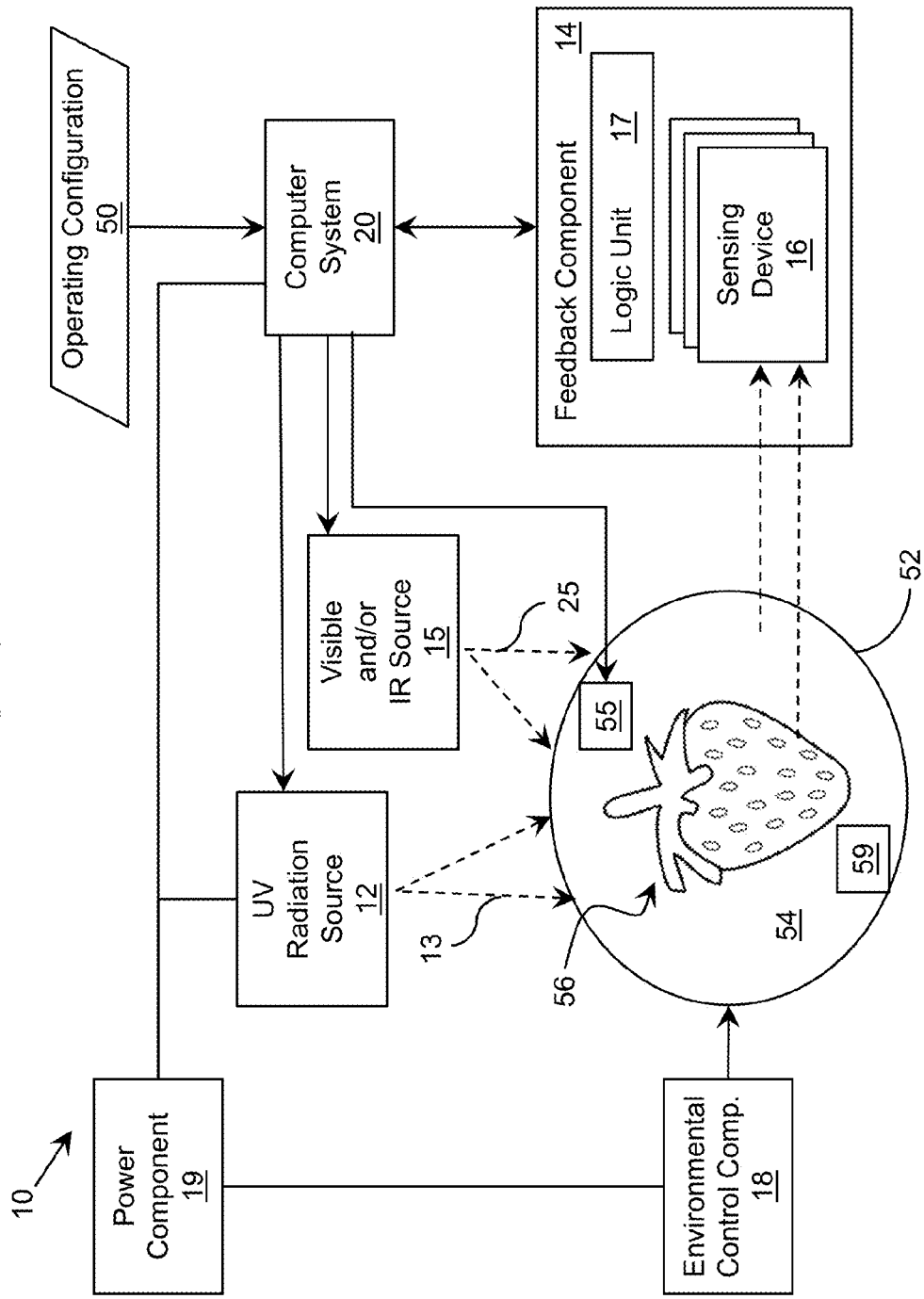
FIG. 3 shows an illustrative system including an ultraviolet radiation system according to an embodiment.

FIG. 3 shows an illustrative system including an ultraviolet radiation system 10 according to an embodiment. The computer system 20 is configured to control the ultraviolet radiation source 12 to direct ultraviolet radiation 13 into a storage area 54 of a storage device 52, within which a set of items 56 are located. The feedback component 14 is configured to acquire data used to monitor a set of current conditions of the storage area 54 and/or the items 56 over a period of time. As illustrated, the feedback component 14 can include a plurality of sensing devices 16, each of which can acquire data used by the computer system 20 to monitor the set of current conditions.

In an embodiment, the sensing devices 16 include at least one of a visual camera or a chemical sensor. The visual camera can acquire data (e.g., visual, electronic, and/or the like) used to monitor the storage area 54 and/or one or more of the items 56 located therein, while the chemical sensor can acquire data (e.g., chemical, electronic, and/or the like) used to monitor the storage area 54 and/or one or more of the items 56 located therein. The set of current conditions of the storage area 54 and/or items 56 can include the color or visual appearance of the items 56, the presence of microorganisms within the storage area 54, and/or the like. In an embodiment, the visual camera comprises a fluorescent optical camera. In this case, when the computer system 20 is operating the UV radiation source 12 in the storage life preservation operating configuration 50A (FIG. 2), the visual camera can be operated to detect the presence of microorganisms as they fluoresce in the ultraviolet light. In an embodiment, the chemical sensor is an infrared sensor, which is capable of detecting any combination of one or more gases, such as ethylene, ethylene oxide, and/or the like. However, it is understood that a visual camera and a chemical sensor are only illustrative of various types of sensors that can be implemented. For example, the sensing devices 16 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the storage area 54 and/or items 56 located therein. In the ethylene decomposition operating configuration 50C, the storage device 52 can include a high efficiency ethylene destruction chamber 55 that includes a high UV reflectivity, high UV intensity radiation chamber for chemical (e.g., ethylene) destruction. In this embodiment, the computer system 20 can operate the one or more devices in the chamber 55 to destroy ethylene, which may be present within the atmosphere of the storage area 54. The computer system 20 can separately monitor the ethylene levels and the level of microorganism activity.

The feedback component 14 also can include one or more additional devices. For example, the feedback component 14 is shown including a logic unit 17. In an embodiment, the logic unit 17 receives data from a set of sensing devices 16 and provides data corresponding to the set of conditions of the storage area 54 and/or items 56 located in the storage area 54 for processing by the computer system 20. In a more particular embodiment, the computer system 20 can provide information corresponding to the currently selected operating configuration 50 for use by the feedback component 14. For example, the logic unit 17 can adjust the operation of one or more of the sensing devices 16, operate a unique subset of the sensing devices 16, and/or the like, according to the currently selected operating configuration 50. In response to data received from the feedback component 14, the computer system 20 can automatically adjust and control one or more aspects of the ultraviolet radiation 13 generated by the ultraviolet radiation source 12 according to the currently selected operating configuration 50.

In an embodiment, the system 10 can include visible and/or infrared (IR) sources 15 which can be controlled by the computer system 20 to generate light 25 directed within the storage area 54. For example, the computer system 20 can control the visible source 15 to generate light 25 with wavelengths configured to increase photosynthesis in one or more food items 56. Additionally, the computer system 20 can control the IR source 15 to generate light 25 directed onto certain foods to locally increase the temperature of the food items 56. The visible and/or IR source 15 also can generate light 25 to excite fluorescence from microorganisms that may be present on items 56, so that a sensing device 16 of the feedback component 14 can detect the microorganisms. Furthermore, the visible and/or IR source 15 can generate light 25 to facilitate a target (e.g., optimal) photocatalytic reaction for the catalyst 59.

As described herein, embodiments can be implemented as part of any of various types of storage systems. FIGS. 4A-4H show illustrative storage devices for use with an ultraviolet radiation system 10 (FIG. 1) according to embodiments. For example, the storage device can be a refrigerator and/or freezer (FIG. 4A) for storing a plurality of food items. Alternatively, the storage device can be a container for biological objects (FIG. 4B). The storage device can be a cooler (FIG. 4C), a backpack (FIG. 4D), a food container (FIG. 4E), a plastic bag (FIG. 4F), a lunchbox (FIG. 4G), a pantry (FIG. 4H, e.g., a shelf in the pantry), and/or the like. In each case, an embodiment of the system 10 can be implemented in conjunction therewith using any solution. To this extent, it is understood that embodiments of the system 10 can vary significantly in the number of devices, the size of the devices, the power requirements for the system, and/or the like. Regardless, it is understood that these are only exemplary storage devices and that the system 10 may be applicable to other storage devices not specifically mentioned herein.

In an embodiment, the ultraviolet radiation source 12 can include a plurality of ultraviolet light emitters located in various locations adjacent to a storage area. To this extent, FIG. 5 shows a partial cross-sectional perspective view of an illustrative storage device 152 according to an embodiment. The storage device 152 includes a storage area 154 for containing at least one item 56. As shown in the figure, a plurality of ultraviolet radiation emitters 12 are located within the storage area 154. The storage device 152 can be comprised of multiple layers. The layers can protect other storage areas and/or components of the storage device 152 from ultraviolet radiation and/or increase the efficiency of the ultraviolet radiation within the storage area 154. The layers do not allow UV radiation to escape from the storage area 154. For example, an ultraviolet transparent wall 57 can surround the storage area 154 within which the ultraviolet radiation emitters 12 are located. A hollow region 58 can be located between the ultraviolet transparent wall 57 and a highly reflective wall 64.

The highly reflective wall 64 can reflect and/or absorb the UV radiation. The highly reflective wall can include a reflectivity of more than approximately 50% as measured for the UV radiation at the normal incidence direction. Approximately 20% of the volume of the hollow region 58 can include a refractive index lower than that of the ultraviolet transparent wall 57. A plurality of elements 60 can protrude from the ultraviolet transparent wall 57 into the hollow region 58. The plurality of elements 60 can include high/low index interfaces 62. During operation, once the ultraviolet radiation emitters 12 shine ultraviolet light into the storage area 154, the high/low index interfaces 60 and the highly reflective wall 64 reflect ultraviolet light back into the storage area 154. The ultraviolet transparent wall 57 can be made of one or more materials that allow ultraviolet radiation to pass through, such as fused silica, an amorphous fluoroplastic (e.g., Teflon by Dupont), and/or the like. Other illustrative materials include alumina sol-gel glass, alumina aerogel, sapphire, aluminum nitride (e.g., single crystal aluminum nitride), boron nitride (e.g., single crystal boron nitride), and/or the like. The outer reflective wall 64 can be made of one or more materials that reflects ultraviolet radiation, such as polished aluminum, a highly ultraviolet reflective expanding polytetrafluoroethylene (ePTFE) membrane (e.g., GORE® Diffuse Reflector Material), and/or the like.

Figure 6:
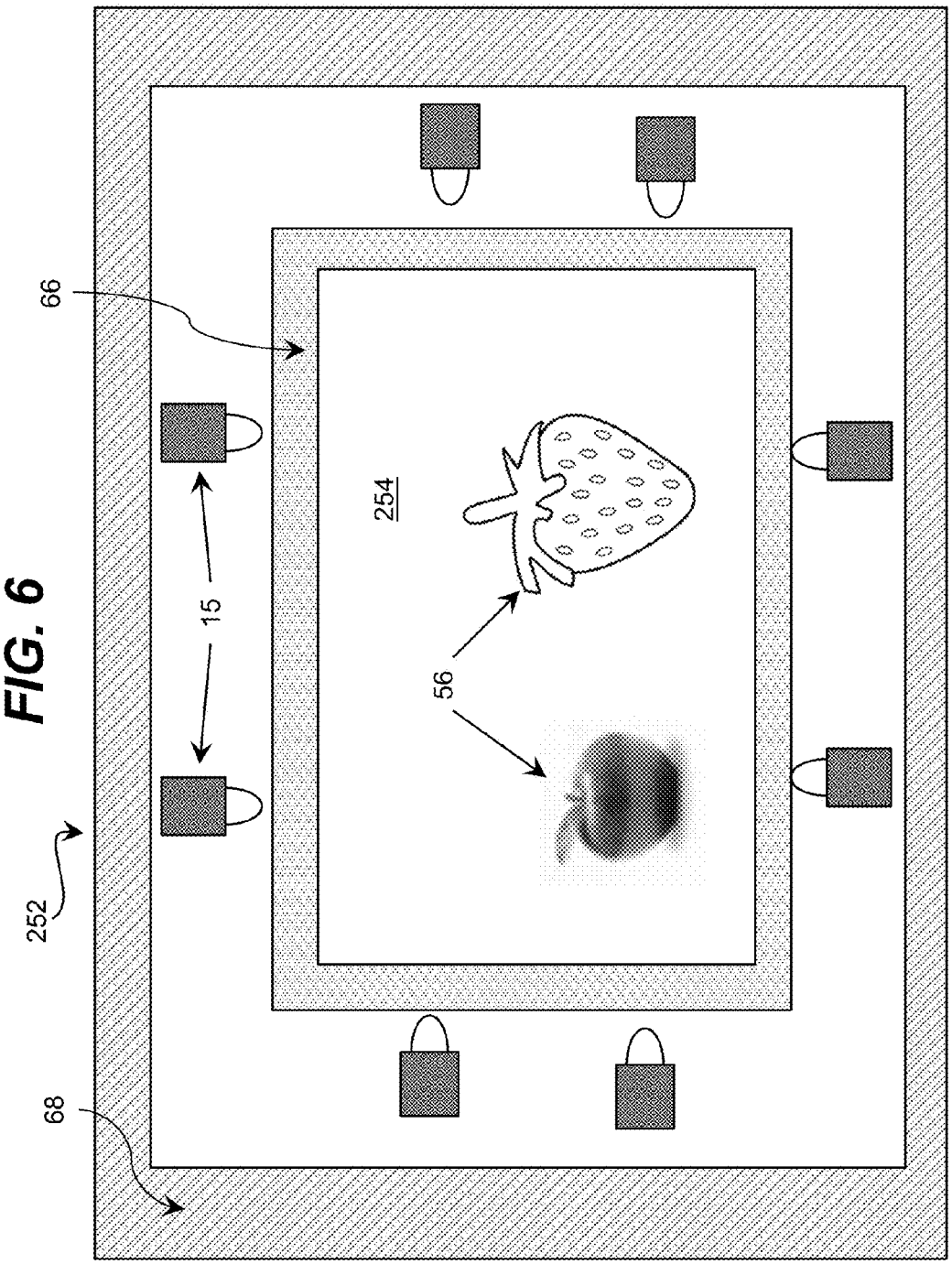
FIG. 6 shows a cross-sectional view of an illustrative storage device according to an embodiment.

FIG. 6 shows a cross-sectional view of another illustrative storage device 252 according to an embodiment. The storage device 252 is shown including an inner ultraviolet radiation transparent enclosure 66 surrounding a storage area 254. The inner ultraviolet radiation transparent enclosure 66 allows ultraviolet radiation emitted from ultraviolet radiation emitters 12 to reach items 56 located within the storage area 254. An outer ultraviolet radiation reflective wall 66 surrounds the inner ultraviolet radiation transparent enclosure 66 and blocks the ultraviolet radiation from exiting the storage device 252. The ultraviolet radiation emitters 12 can be located between the inner ultraviolet radiation transparent enclosure 66 and the outer ultraviolet radiation reflective wall 68.

Figure 7A:
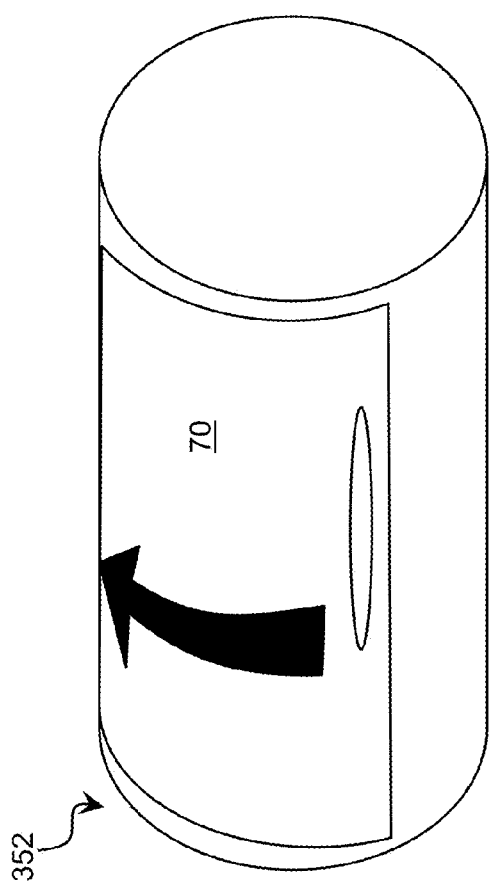
FIGS. 7A and 7B show perspective views of illustrative storage devices according to embodiments.
Figure 7B:
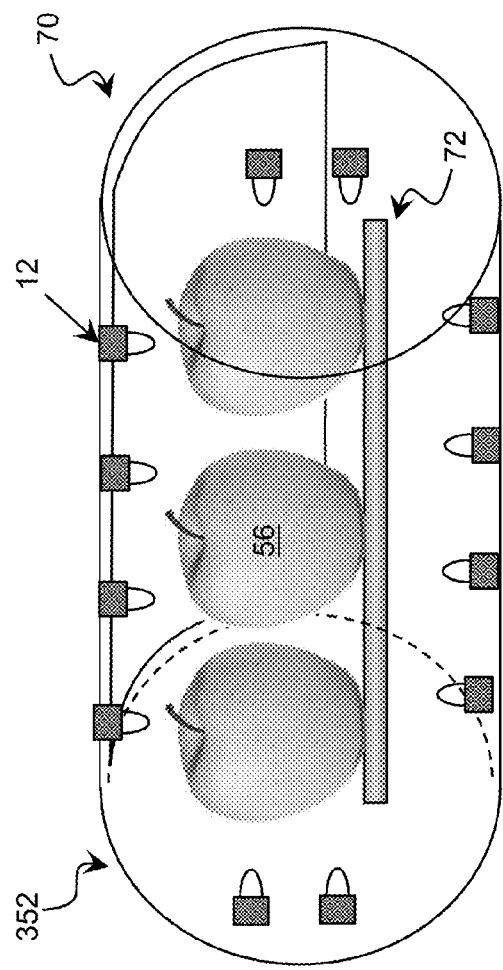

FIGS. 7A and 7B show a perspective view of illustrative storage devices 352 according to other embodiments. In this case, each storage device 352 is shown as having a cylindrical shape. The cylindrical shape for the storage device 352 can allow for increased reflectivity of ultraviolet radiation back into the storage area 354 and onto the stored items from various sides/angles. Furthermore, the cylindrical shape can increase the surface area of items 56 that are exposed to ultraviolet radiation. The cylindrical shaped storage device 352 can be utilized to store, for example, medium sized round food items, such as apples, tomatoes, and/or the like. However, it is understood that the storage device 352 can include any shape and size. The storage device 352 in FIGS. 7A and 7B includes a sliding door 70 for access to the storage area within which items 56 may be located.

A computer system 20 (FIG. 1) can be configured to control the ultraviolet radiation sources 12, such that when sliding door 70 is opened, the ultraviolet radiation sources 12 are turned off. Once sliding door 70 is closed, the ultraviolet radiation sources 12 are turned back on. Although not shown, the storage device 352 may also include an inner ultraviolet radiation transparent enclosure and an outer ultraviolet radiation reflective wall, as shown and described herein. Furthermore, the storage device 352 can include a shelf 72 for the items 56. In an embodiment, the shelf 72 is formed of an ultraviolet radiation transparent material so that the items 56 located on the shelf 72 can be subjected to ultraviolet radiation from any direction. FIG. 8 shows a cross-sectional view of an illustrative storage device 452 according to an embodiment. In this case, the storage device 452 includes a plurality of ultraviolet radiation transparent shelves 472 for a plurality of items 56. The shelves 472 can be entirely or only partially located within the storage device 452. Additionally, the ultraviolet radiation sources 12 can be located within each of the ultraviolet radiation transparent shelves 472.

FIGS. 9A and 9B show cross-sectional views of illustrative storage devices 552, 652, respectively, according to still other embodiments. In this case, the plurality of ultraviolet radiation transparent shelves 572, 672, respectively, include a plurality of dimensioned depressions 74. The dimensioned depressions 74 can be sized for any desired item to be stored thereon. For example, in FIG. 9A, the dimensioned depressions 74 are sized for strawberries 54. In FIG. 9B, the dimensioned depressions 74 are sized for blueberries 54. The dimensioned depressions 74 can also be sized, for example, for raspberries, kiwi fruit, broccoli, cauliflower, and/or the like. While each shelf 572, 672 is shown having multiple depressions of the same size, it is understood that a shelf 572, 672 can have any number of depressions of any of various sizes. The dimensioned depressions 74 can be configured to increase an amount of power of the ultraviolet radiation directed onto the item(s) stored therein. For example, a transparent depression can allow ultraviolet light to pass through the sides of the depression directed toward the stored item. Additionally, the depressions can prevent the stored items from touching one another, thereby increasing an amount of the surface area that can be illuminated by ultraviolet radiation.

FIG. 10 shows a perspective view of an illustrative storage device 752 according to an embodiment. In this embodiment, the storage device 752 can include a plurality of sub-compartments that are individually/separately monitored by the computer system 20 (FIG. 1) using the feedback component 14 (FIG. 1). It is understood that the plurality of sub-compartments can be located within an inner ultraviolet radiation transparent enclosure, such as the enclosure 66 shown in FIG. 6. Furthermore, the ultraviolet radiation sources 12 in each sub-compartment can be individually controlled by the computer system 20. For example, a shelf 772 can be partitioned into a first sub-compartment 76 and a second sub-compartment 78, which are separated by a divider 80. Each of the plurality of sub-compartments 76, 78 can include the same type of UV sources 12.

Alternatively, as shown in FIG. 10, the first sub-compartment 76 can include a first type of UV source 12A, and the second sub-compartment 78 can include a second type of UV source 12B. The computer system 20 can control the UV sources 12A, 12B, such that the first sub-compartment 76 is subjected to a first operating configuration and the second sub-compartment 78 is subjected to a second operating configuration. The particular operating configuration for each sub-compartment can differ. Furthermore, the computer system 20 can control the UV source 12A to have a first intensity and a first wavelength, and control the UV source 12B to have a second intensity and a second wavelength. For example, the UV source 12A can include a full intensity, while the UV source 12B includes a zero intensity. Conversely, the UV source 12A can include a zero intensity, while the UV source 12B includes a full intensity. Furthermore, the computer system 20 can independently tune the relative intensities of each UV source 12A, 12B, and either UV source 12A, 12B can have any intensity between zero and full.

Additionally, the shelves 772 may revolve, e.g., via a motor 80. The motor 80 may be controlled by the computer system 20 and rotate according to a timing schedule, such that the first sub-compartment 76 and the second sub-compartment 78 each receive ultraviolet light emitted by one of the UV sources 12A, 12B according to a particular operating configuration at a specific time. Although UV sources 12A, 12B are shown as mounted above the shelf 772, it is understood that UV sources can also be within the shelf 772, below the shelf 772, and/or the like.

FIG. 11 shows a perspective view of another illustrative storage device 852 according to an embodiment. The storage device 852 can be attached to a gyroscopic suspension 82 so that the storage device 852 rotate can rotate. As the storage device 852 rotates, ultraviolet radiation from ultraviolet radiation sources 12 can thoroughly illuminate any items located within the storage device 852 from all angles.

Returning to FIG. 3, it is understood that the system 10 may include a power component 19 that is implemented separately from the storage device 52 to supply power to one or more of the various components of system 10, such as ultraviolet radiation sources 12, motor 80 (FIG. 10), feedback component 14, computer system 20, and/or the like. For example, the storage device 52 may comprise a cooler or the like, which does not include or otherwise require any power source. Furthermore, the storage device 52 may comprise a power source that is insufficient to operate the various devices of system 10 in addition to maintaining one or more aspects of the environment within the storage area 54 for a desired period of time. Regardless, the power component 19 can be utilized to operate system 10. The power component 19 can comprise any source of power including, but not limited to, the power grid, a battery set, an automotive charger, a solar cell, and/or the like. In an embodiment, the computer system 20 can implement multiple modes of operation depending on the source of power. In particular, when a power component 19 of limited capacity is being utilized, one or more functions of system 10 can be disabled and/or reduced to lengthen an operating time for system 10. For example, use of ultraviolet radiation source 12 to prolong the life of items within the storage area 54 or disinfect the storage area 54 by generating a higher intensity of ultraviolet radiation can be disabled.

An environment within the storage area 54 can be controlled by an environmental control component 18. In an illustrative implementation, the environmental control component 18 can comprise a temperature control module, a humidity control module, and/or a convection control module. During normal operation of the environmental control component 18, a user 6 (FIG. 1) (e.g., using external interface component 26B) can select a desired temperature, humidity, and/or the like, to maintain within storage area 54. The environmental control component 18 can subsequently operate one or more cooling/heating components of temperature control module to maintain the desired temperature, operate one or more humidifying/dehumidifying components of humidity control module to maintain the desired humidity, operate one or more air or fluid convection components (e.g., fan, pump, vent, valve, etc.) of convection control module to assist in maintaining a relatively even temperature/humidity within storage area 54, and/or the like. Alternatively, local temperature control within storage area 54 can be maintained by cool air recirculation that is controlled by the environmental control component 18.

The computer system 20 can be configured to adjust one or more operating parameters of the environmental control component 18 based on a set of current conditions in the storage area 54 and/or an operating configuration of the UV radiation source 12. For example, the computer system 20 can adjust one or more of: a temperature, a humidity, a gas convection, and/or a fluid convection of the storage area 54 in response to a set of biological activity dynamics and according to a currently selected operating configuration. To this extent, each operating configuration can further define a set of target environmental conditions for use during the UV illumination. Such environmental conditions can include a target temperature, a target humidity, additional illumination by non-ultraviolet sources (e.g., visible, infrared), air circulation, and/or the like, Furthermore, one or more of the environmental conditions can change over time during implementation of the operating configuration. In an illustrative embodiment, the computer system 20 can operate the environmental control component 18 to circulate air into the chamber 55, e.g., during implementation of the ethylene decomposition operating configuration. Furthermore, the set of current conditions in the storage area 54 can include an operating condition of one or more components of the system 10, such as the ultraviolet radiation source(s) 12. Information regarding the operating condition can be used to, for example, notify a user 6 of a problem using the alarm component 23, alter one or more aspects of an operating configuration, and/or the like. Additionally, the set of current conditions in the storage area 54 can include data corresponding to a dose of ultraviolet radiation delivered by an ultraviolet radiation source 12 during a predetermined time period. In this case, the computer system 20 can dynamically determine when to turn off the ultraviolet radiation source 12.

It is understood that the set of current conditions in the storage area 54 can include one or more attributes corresponding to a set of biological activity dynamics present within the storage area. The set of biological activity dynamics can include, for example, a presence of biological activity (e.g., exponential bacterial growth), a location of the biological activity, a type of biological activity (e.g., type of organism), a concentration of the biological activity, an estimated amount of time an organism has been in a growth phase (e.g., exponential growth and/or stationary), and/or the like. The set of biological activity dynamics can include information on the variation of the biological activity over time, such as a growth rate, a rate with which an area including the biological activity is spreading, and/or the like. In an embodiment, the set of biological activity dynamics are related to various attributes of bacteria activity within an area, including, for example, the presence of detectable bacteria activity, measured bacteria population/concentration time dynamics, growth phase, and/or the like.

As described herein, aspects of the invention can be implemented to treat (e.g., preserve, disinfect, and/or the like) various types of food stored in various types of environments. A typical environment can comprise a refrigerated environment, in which food is frequently stored to extend the shelf life of the food. However, embodiments can be implemented in other non-refrigerated environments, in which food is stored for a period of time, e.g., to ripen, prior to being used, and/or the like. Furthermore, an embodiment can be implemented in conjunction with a freezer, in which the temperature is maintained well below the freezing point of water. To this extent, the types of food items to which aspects of the invention can be implemented can include various types of food as described herein. As described herein, the foods can include various types of fruits and vegetables. However, the foods also can include frozen consumables, such as ice cubes, ice cream, and/or the like. Furthermore, the foods can include liquids, grains, cereals, and/or the like. Additionally, as described herein, embodiments can be implemented to treat non-food items stored in any type of environment. Such non-food items can include, for example, frozen/liquid chemicals, sand, wood, and/or the like. Regardless, it is understood that a treated item can be ultraviolet transparent (e.g., semi-transparent), ultraviolet absorbing, and/or ultraviolet reflective.

In an embodiment, the computer system 20 can be configured to operate the UV radiation source 12 (e.g., during the storage life preservation operating configuration 50A) to generate ultraviolet radiation to, for example, maintain and/or increase natural phenols, including one or more types of flavonoids, in the food items 56 within the storage area 54. In this case, the computer system 20 can increase the nutritional qualities, including antioxidant benefits, and/or increase storage life of the food items 56.

While shown and described herein as a method and system for managing a storage area, it is understood that aspects of the invention further provide various alternative embodiments. For example, in one embodiment, the invention provides a computer program fixed in at least one computer-readable medium, which when executed, enables a computer system to manage the storage area using a process described herein. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing the storage area. In this case, the generating can include configuring a computer system, such as the computer system 20 (FIG. 1), to implement a method of managing the storage area as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
   at least one ultraviolet radiation source configured to generate ultraviolet radiation directed within a storage area; and
   a control system for controlling ultraviolet radiation generated by the at least one ultraviolet radiation source using one of a plurality of selectable operating configurations and a set of current conditions of at least one of: the storage area or a set of items located in the storage area, wherein the controlling includes adjusting at least one of: a direction, an intensity, a pattern, or a spectral power of ultraviolet radiation directed within the storage area based on the set of current conditions of the storage area and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration, wherein the storage life preservation operating configuration is configured to increase a storage lifespan of the set of items, the disinfection operating configuration is configured to sterilize microorganisms present on the set of items, and the ethylene decomposition operating configuration is configured to remove ethylene emitted from the set of items.

2. The system of claim 1, further comprising a monitoring system for monitoring at least one of: a set of current biological conditions of the storage area or an operating condition of the at least one ultraviolet radiation source.

3. The system of claim 2, further comprising at least one of: an optical sensor, a chemical sensor, or a mechanical sensor for providing the monitoring system data corresponding to at least one of the set of current conditions.

4. The system of claim 1, wherein the each of the plurality of selectable operational configurations includes a unique combination of: a target intensity, a target peak wavelength, and a target pattern for the ultraviolet radiation generated by the at least one ultraviolet radiation source, wherein the target pattern includes at least one of: a duration or a duty cycle for a plurality of ultraviolet illuminations.

5. The system of claim 1, wherein the storage area further comprises:
   an inner ultraviolet radiation transparent enclosure configured to contain a plurality of stored items; and
   an outer ultraviolet radiation reflective wall surrounding the inner ultraviolet radiation transparent enclosure.

6. The system of claim 5, further comprising a plurality of ultraviolet radiation transparent shelves at least partially located within the inner ultraviolet radiation transparent enclosure.

7. The system of claim 6, wherein each of the plurality of ultraviolet radiation transparent shelves includes a plurality of dimensioned depressions for supporting the plurality of stored items.

8. The system of claim 6, wherein each of the plurality of ultraviolet radiation transparent shelves includes at least one ultraviolet radiation source.

9. The system of claim 5, further comprising a plurality of sub-compartments within the inner ultraviolet radiation transparent enclosure, wherein a first sub-compartment includes a first operating configuration of the plurality of selectable operating configurations and a second sub-compartment includes a second operating configuration of the plurality of selectable operating configurations distinct from the first operating configuration.

10. The system of claim 1, wherein the storage area is a storage area of a refrigeration device configured to store at least one refrigerated item.

11. The system of claim 1, further comprising:
   a set of visible and infrared radiation sources; and
   a feedback component including a set of sensing devices configured to sense the set of current conditions, the set of current conditions including a visual attribute of the set of items and a set of chemical attributes of the set of items, wherein the visual attribute and the set of chemical attributes are used by the control system to control the at least one ultraviolet radiation source and the set of visible and infrared radiation sources, and wherein the set of chemical attributes include a presence of ethylene gas.

12. A food storage device comprising:
a storage area configured to store at least one perishable food item;
at least one ultraviolet radiation source configured to generate ultraviolet radiation directed within the storage area;
a monitoring system for monitoring a set of current conditions of at least one of: the storage area or a set of items located in the storage area, wherein the set of current conditions includes a set of current biological conditions of the storage area and an operating condition of the at least one ultraviolet radiation source; and
a control system for controlling the ultraviolet radiation generated by the at least one ultraviolet radiation source using one of a plurality of selectable operating configurations and the set of current conditions, wherein the controlling includes adjusting at least one of: a direction, an intensity, a pattern, or a spectral power of ultraviolet radiation directed within the storage area based on the set of current conditions and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration, wherein the storage life preservation operating configuration is configured to increase a storage lifespan of the set of items, the disinfection operating configuration is configured to sterilize microorganisms present on the set of items, and the ethylene decomposition operating configuration is configured to remove ethylene emitted from the set of items.

13. The storage device of claim 12, further comprising at least one of: an optical sensor, a chemical sensor, or a mechanical sensor for providing the monitoring system data corresponding to at least one of the set of current conditions.

14. The storage device of claim 12, wherein each of the plurality of selectable operational configurations includes a unique combination of: a target intensity, a target peak wavelength, and a target pattern for the ultraviolet radiation generated by the at least one ultraviolet radiation source.

15. The storage device of claim 12, wherein the control system is configured to turn off all of the at least one ultraviolet radiation source in response to the storage area being opened.

16. The storage device of claim 12, wherein the storage area further comprises:
an inner ultraviolet radiation transparent enclosure configured to contain a plurality of perishable food items; and
an outer ultraviolet radiation reflective wall surrounding the inner ultraviolet radiation transparent enclosure.

17. The storage device of claim 16, further comprising a plurality of ultraviolet radiation transparent shelves at least partially located within the inner ultraviolet radiation transparent enclosure, wherein the plurality of ultraviolet radiation transparent shelves include dimensioned depressions for supporting the plurality of perishable food items.

18. The storage device of claim 17, wherein each of the plurality of ultraviolet radiation transparent shelves includes at least one ultraviolet radiation source.

19. A refrigeration device comprising:
a storage area configured to store at least one refrigerated item;
a component configured to control at least one environmental condition of the storage area, wherein the at least one environmental condition includes at least one of: a temperature, a humidity, a gas convection, or a fluid convection;
at least one ultraviolet radiation source configured to generate ultraviolet radiation directed within the storage area; and
a monitoring and control system for managing the storage area by performing a method comprising:
monitoring a set of current conditions of at least one of: the storage area or a set of items located in the storage area; and
controlling ultraviolet radiation generated by the at least one ultraviolet radiation source using one of a plurality of selectable operating configurations and the set of current conditions, wherein the controlling includes adjusting at least one of: a direction, an intensity, a pattern, or a spectral power of ultraviolet radiation directed within the storage area based on the set of current conditions of the storage area and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration, wherein the storage life preservation operating configuration is configured to increase a storage lifespan of the set of items, the disinfection operating configuration is configured to sterilize microorganisms present on the set of items, and the ethylene decomposition operating configuration is configured to remove ethylene emitted from the set of items.

20. The device of claim 19, further comprising at least one of: an optical sensor, a chemical sensor, or a mechanical sensor for providing the monitoring and control system data corresponding to at least one of the set of current conditions.

21. The device of claim 19, wherein each of the plurality of selectable operational configurations includes a unique combination of: a target intensity, a target peak wavelength, and a target pattern for the ultraviolet radiation generated by the at least one ultraviolet radiation source.

22. The device of claim 19, wherein the storage area further comprises:
an inner ultraviolet radiation transparent enclosure configured to contain a plurality of refrigerated items; and
an outer ultraviolet radiation reflective wall surrounding the inner ultraviolet radiation transparent enclosure.

23. The device of claim 19, wherein the component configured to control is a freezer, and wherein the at least one refrigerated item is a frozen item.

* * * * *

UNITED STATES PATENT AND TRADEMARK OFFICE
CERTIFICATE OF CORRECTION

PATENT NO.       : 9,034,271 B2
APPLICATION NO.  : 14/012682
DATED            : May 19, 2015
INVENTOR(S)      : Shur et al.

Page 1 of 1

It is certified that error appears in the above-identified patent and that said Letters Patent is hereby corrected as shown below:

On the title page, in the Assignee, item 73, delete "Sensor Electronics Technology, Inc." and insert --Sensor Electronic Technology, Inc.--.

Signed and Sealed this
Twenty-ninth Day of September, 2015

Michelle K. Lee
*Director of the United States Patent and Trademark Office*